United States Patent
Gupta

(10) Patent No.: US 11,752,145 B2
(45) Date of Patent: Sep. 12, 2023

(54) QUINOLINE DERIVATIVES WITH OTHER ANTI-VIRAL AGENTS

(71) Applicant: Sanjay Gupta, Voorhees, NJ (US)

(72) Inventor: Sanjay Gupta, Voorhees, NJ (US)

(*) Notice: Subject to any disclaimer, the term of this patent is extended or adjusted under 35 U.S.C. 154(b) by 81 days.

(21) Appl. No.: 17/217,270

(22) Filed: Mar. 30, 2021

(65) Prior Publication Data

US 2021/0299120 A1   Sep. 30, 2021

Related U.S. Application Data

(60) Provisional application No. 63/002,250, filed on Mar. 30, 2020.

(51) Int. Cl.
| | | |
|---|---|---|
| *A61K 45/06* | (2006.01) | |
| *A61K 31/49* | (2006.01) | |
| *A61K 31/4706* | (2006.01) | |
| *A61K 31/47* | (2006.01) | |
| *A61K 31/4704* | (2006.01) | |
| *A61K 31/4709* | (2006.01) | |
| *A41D 13/11* | (2006.01) | |
| *A61K 9/00* | (2006.01) | |

(52) U.S. Cl.
CPC .......... *A61K 31/49* (2013.01); *A41D 13/1192* (2013.01); *A61K 9/0043* (2013.01); *A61K 9/0053* (2013.01); *A61K 9/0073* (2013.01); *A61K 31/4706* (2013.01); *A61K 45/06* (2013.01)

(58) Field of Classification Search
CPC .............. A41D 13/1192; A61K 9/0043; A61K 9/0053; A61K 9/0073; A61K 45/06; A61K 31/49; A61K 31/4706; A61K 31/47; A61K 31/4704
See application file for complete search history.

(56) References Cited

U.S. PATENT DOCUMENTS 7,288,265 B1 * 10/2007 Rolf .................... A61F 13/0209
424/443

\* cited by examiner

*Primary Examiner* — Brenda L Coleman
(74) *Attorney, Agent, or Firm* — Jonathan D. Ball; Greenberg Traurig, LLP

(57) ABSTRACT

Compositions and methods for the treatment or prophylaxis of viral and other infections (e.g., coronavirus) are provided. The compositions typically comprise a quinoline derivative and an additional anti-viral agent. Incorporations of these agents into fabrics for use as filtration devices which forestall infection is also disclosed.

13 Claims, No Drawings

QUINOLINE DERIVATIVES WITH OTHER ANTI-VIRAL AGENTS

CROSS REFERENCE TO RELATED APPLICATIONS

The present application claims the benefit of and priority to under 35 U.S.C. § 119 to U.S. App. No. 63/002,250, filed Mar. 30, 2020, the entire contents of which are hereby incorporated by reference in their entirety.

FIELD OF DISCLOSURE

The present disclosure is related to combinations of active agents for the treatment or prophylaxis of viral and other infections.

BACKGROUND

Viral infections often lead to serious medical conditions in infected patients. In particular, respiratory viruses such as coronaviruses may lead to fever, swollen adenoids (resulting in sore throat) at lower viral loads. Following replication within a host, and as the viral load increases, the infected subject may contract more severe conditions such as pneumonia, bronchitis, and, in some cases. In some cases, subjects with high viral loads contract sever acute respiratory syndrome (SARS), which causes both upper and lower tract respiratory infections. Robust treatments available for these infections are lacking which further allows for the infection spread.

It is therefore an object of this disclosure to provide compositions and methods for the treatment or prophylaxis of viral infections.

SUMMARY

In accordance with the foregoing objectives and others, the present disclosure provides pharmaceutical compositions for the treatment or prophylaxis of viral infections. In some embodiments, the pharmaceutical compositions are effective at reducing the viral load in the subject or preventing the increase of the viral load in the subject. These reductions in viral may prevent the development of more serious conditions associated with the of infection (e.g., diseases, disorders, or conditions with an etiology connected to the viral infection or for example a high viral load of the infection).

The pharmaceutical composition may comprise one or more pharmaceutically acceptable carrier, diluents, or excipients and a therapeutically effective amount of a quinoline derivative and optionally an anti-viral agent;
wherein the anti-viral agent is selected from pyrithione, hinokitiol, tetracycline, doxycycline, azithromycin, and zinc (e.g., zinc, compounds comprising zinc, $ZnO_2$); or tautomers, enantiomers, mixtures of enantiomers, racemates, thereof; or prodrugs thereof, or pharmaceutically acceptable salts of any of the foregoing. In some embodiments, the pharmaceutical composition is an oral composition or a nasal composition. The quinoline derivative may be selected from, for example, chloroquine, hydroxychloroquine, quinine, or quinidine enantiomers, mixtures of enantiomers, racemates, thereof; or prodrugs thereof, or pharmaceutically acceptable salts of any of the foregoing. In some embodiments, the pharmaceutical composition may be a composition to be added to a food product such as a powder or tablet.

In some embodiments, the pharmaceutical composition is a nasal or oral inhalation product Fabrics are also provided comprising a quinoline derivative and/or an anti-viral agent. These agents may be impregnated into the fabric. For example, an untreated fabric may be submerged in a solution comprising one or more of the quinoline derivatives and/or anti-viral agents in order to impregnate the fabric with the active material(s). The fabric may be then be dried to remove any residual solvent from the solution. In various embodiments, the anti-viral agent is selected from pyrithione, hinokitiol, tetracycline, doxycycline, azithromycin, and zinc; or tautomers, enantiomers, mixtures of enantiomers, racemates, thereof; or prodrugs thereof, or pharmaceutically acceptable salts of any of the foregoing. The quinoline derivative may be selected from, for example, chloroquine, hydroxychloroquine, quinine, or quinidine enantiomers, mixtures of enantiomers, racemates, thereof; or prodrugs thereof, or pharmaceutically acceptable salts of any of the foregoing.

The fabric may also be used in a composite fabric. For example, the composite fabric may comprise the anti-viral and/or quinoline treated derivative fabric and one or more other layers attached thereto. In certain embodiments, the composite fabric has a waterproof layer (e.g., a polyurethane layer) attached to one surface and/or a breathable woven textile attached to a surface (e.g., the surface opposite the waterproof layer).

Facemasks (e.g., N95 facemasks) are also disclosed having a breathing piece such that air passes through the breathing piece when a user is breathing; wherein the breathing piece comprises one or more fabrics as described herein.

Method of use for these devices are also provided. In some embodiments, the method may be for the treatment or prophylaxis of a viral infection or a disease, disorder, or condition associated with the viral infection in a subject in need thereof and may comprise administration of the pharmaceutical composition.

Additionally, methods of preventing the increase in the viral load in a subject in need thereof may comprise providing an anti-viral agent and/or quinoline derivative treated fabric or a facemask comprising these treated fabrics to the subject, wherein the subject breathes through the fabric thereby reducing the viral load passing into the respiratory system of the subject. In some embodiments, the method of preventing the increase in the viral load in a subject in need thereof may comprise wearing the treated fabric or the facemask comprising the treated fabric, such that wearing the facemask or fabric results in a configuration where the subject breathes through the fabric thereby reducing the viral load passing into the respiratory system of the subject.

Methods for prophylaxis against a respiratory infection are provided which may comprise administering orally or intranasally to a subject in need thereof a pharmaceutical composition comprising a quinoline derivative and optionally an anti-viral agent;
wherein the anti-viral agent is selected from pyrithione, hinokitiol, tetracycline, doxycycline, azithromycin, and zinc; or tautomers, enantiomers, mixtures of enantiomers, racemates, thereof; or prodrugs thereof, or pharmaceutically acceptable salts of any of the foregoing.

In some embodiments, the method for prophylaxis against an infection may comprise administering via mucosal or other body surfaces to a subject in need thereof a pharmaceutical composition comprising a quinoline derivative and an anti-viral agent;

wherein the anti-viral agent is selected from pyrithione, hinokitiol, tetracycline, doxycycline, azithromycin, and zinc; or tautomers, enantiomers, mixtures of enantiomers, racemates, thereof; or prodrugs thereof, or pharmaceutically acceptable salts of any of the foregoing. Exemplary, mucosal or other body surfaces include the eyes, ear canal, anus, and vagina.

DETAILED DESCRIPTION

Detailed embodiments of the present disclosure are disclosed herein; however, it is to be understood that the disclosed embodiments are merely illustrative of the disclosure that may be embodied in various forms. In addition, each of the examples given in connection with the various embodiments of the disclosure is intended to be illustrative, and not restrictive.

All terms used herein are intended to have their ordinary meaning in the art unless otherwise provided. All concentrations are in terms of percentage by weight of the specified component relative to the entire weight of the topical composition, unless otherwise defined.

As used herein, "a" or "an" shall mean one or more. As used herein when used in conjunction with the word "comprising," the words "a" or "an" mean one or more than one. As used herein "another" means at least a second or more.

As used herein, all ranges of numeric values include the endpoints and all possible values disclosed between the disclosed values. The exact values of all half integral numeric values are also contemplated as specifically disclosed and as limits for all subsets of the disclosed range. For example, a range of from 0.1% to 3% specifically discloses a percentage of 0.1%, 1%, 1.5%, 2.0%, 2.5%, and 3%. Additionally, a range of 0.1 to 3% includes subsets of the original range including from 0.5% to 2.5%, from 1% to 3%, from 0.1% to 2.5%, etc. It will be understood that the sum of all weight % of individual components will not exceed 100%.

Throughout this description, various components may be identified having specific values or parameters, however, these items are provided as exemplary embodiments. Indeed, the exemplary embodiments do not limit the various aspects and concepts of the present disclosure as many comparable parameters, sizes, ranges, and/or values may be implemented. Unless otherwise specified, the terms "first," "second," and the like, "primary," "secondary," and the like, do not denote any order, quantity, or importance, but rather are used to distinguish one element from another.

By "consist essentially" it is meant that the ingredients include only the listed components along with the normal impurities present in commercial materials and with any other additives present at levels which do not affect the operation of the disclosure, for instance at levels less than 5% by weight or less than 1% or even 0.5% by weight.

A pharmaceutical composition is typically a composition containing one or more active compounds (e.g., quinoline derivatives, antiviral agents, etc.) described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gel cap, etc.); for topical administration (e.g., as a cream, gel, lotion, tonic, ointment, etc.). In various implementations, the pharmaceutical composition may be a dosage form in the form of a spray, ointment, foams, heated steam, aerosol, liquid drops, mouthwash, rinse, or tonic. In some embodiments, the pharmaceutical composition may be a nasal dosage form for nasal application in the form of a nasal spray, ointment, foam, heated steam, aerosol, or liquid drops. In some embodiments the pharmaceutical composition may be in the form of an oral dosage form such as a mouthwash, heated steam, mouth rinse, syrup, or tonic. The density of any forms of the invention may be between 0.8 g/mL and 1.2 g/mL, for example between 0.9 g/mL and 1.1 g/mL or between 0.95 g/mL and 1.05 g/mL. In some embodiments, the heated steam for inhalation may be produced by heating an aqueous solution comprising the quinoline derivative and anti-viral agent at a temperature of more than 70° C. or more than 80° C. or more than 90° C. or more than 100° C. or more than 110° C. or more than 115° C. (e.g., 70° C.-150° C., 80° C.-150° C., 90° C.-150° C. 100° C.-150° C., 110° C.-150° C., 115° C., −150° C.) for a time period sufficient to induce vaporization of the aqueous solution and creation of an inhalable medicament.

Pharmaceutical compositions may comprise a base solution. Pharmaceutical compositions in the form of a foam typically comprise a propellant gas or air. The base solution may be mixed with the propellant gas or air at the time of delivery, prior to delivery, or after delivery to the target area (e.g., nasal passage). The base solution may include various compositions including water, salt, fat, milk, oil, proteins, and combinations thereof. Additionally, the base solution may include one or more surfactants such as sodium lauryl ether sulfate (SLES), sodium lauryl sulfate (SLS), ammonium lauryl sulfate (ALS), lecithin, glycerol, TWEEN 20 or TWEEN 80. Nitrous oxide, air, $CO_2$ or other gaseous products may be used to create bubbles in foam compositions, thus allowing substances to fill the intended delivery location (e.g., nasal passageway). Foams may also be made after the quinoline derivatives and anti-viral agents have been delivered. For example, the quinoline derivatives and anti-viral agents may be applied to the target area first in a powdered, dry, or gas treated dry powder form followed by application of the base solution propelled with gas to the target area thus forming a foam in the target area. In some embodiments, the base solution comprises one or more moisturizing agents such as glycerin, aloe vera, hyaluronan, shea butter, milk fat, oil such as olive oil, coconut oil, flaxseed oil, or almond oil. The base solution may be hypertonic or hypotonic.

As used herein, the phrase "pharmaceutically acceptable" generally safe for ingestion or contact with biologic tissues at the levels employed. Pharmaceutically acceptable is used interchangeably with physiologically compatible. It will be understood that the pharmaceutical compositions of the disclosure include nutraceutical compositions (e.g., dietary supplements) unless otherwise specified.

Unit dosage forms, also referred to as unitary dosage forms, often denote those forms of medication supplied in a manner that does not require further weighing or measuring to provide the dosage (e.g., tablet, capsule, caplet, etc.). For example, a unit dosage form may refer to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, and gel cap. In certain embodiments, the compounds described herein, including crystallized forms, polymorphs, and solvates thereof, may be present in a unit dosage form.

Useful pharmaceutical carriers, excipients, and diluents for the preparation of the compositions hereof, can be solids, liquids, or gases. These include any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. Thus, the compositions can take the form of tablets, pills, capsules, suppositories, powders, enterically coated or other protected formulations (e.g., binding on ion-exchange resins or packaging in lipid-protein vesicles), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols are examples of liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, chitosan, talc, glucose, lactose, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for administration to the recipient.

Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols, such as polyethylene glycol and propylene glycol; esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; self-emulsifying drug delivery systems (SEDDS) such as d-atocopherol polyethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids; water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives can also be used to enhance delivery of the compounds described herein.

The compounds described herein may be present as a pharmaceutically acceptable salt. Typically, salts are composed of a related number of cations and anions (at least one of which is formed from the compounds described herein) coupled together (e.g., the pairs may be bonded ionically, etc.) such that the salt is electrically neutral. Pharmaceutically acceptable salts may retain or have similar activity to the parent compound (e.g., an $ED_{50}$ within 10%, etc.) and have a toxicity profile within a range that affords utility in pharmaceutical compositions. For example, pharmaceutically acceptable salts may be suitable for use in contact with the tissues of humans and animals without undue toxicity, irritation, allergic response and are commensurate with a reasonable benefit/risk ratio. Pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecyl sulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxy-ethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

Pharmaceutically acceptable acid addition salts of the disclosure can be formed by the reaction of a compound of the disclosure with an equimolar or excess amount of acid. Alternatively, hemi-salts can be formed by the reaction of a compound of the disclosure with the desired acid in a 2:1 ratio, compound to acid. The reactants are generally combined in a mutual solvent such as diethyl ether, tetrahydrofuran, methanol, ethanol, iso-propanol, benzene, or the like. The salts normally precipitate out of solution within, e.g., one hour to ten days and can be isolated by filtration or other conventional methods.

Solvates of the compounds described herein may the aggregate of the compound or an ion of the compound with one or more solvents. Such solvents may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "effective amount" or "therapeutically effective amount" of one or more agents (e.g., chloroquine, hydroxychloroquine, quinine, quinidine, pyrithione, hinokitiol, tetracycline, doxycycline, azithromycin), as used herein, is that amount sufficient to effect beneficial or desired results, such as clinical results, and, as such, an "effective amount" depends upon the context in which it is being applied. In some embodiments, the compounds are administered in an effective amount for the treatment or prophylaxis of a disease disorder or condition (e.g., a viral infection). In another embodiment, in the context of administering these agents that is an antiviral agent (e.g., chloroquine, hydroxychloroquine, quinine, quinidine, pyrithione, hinokitiol, tetracycline, doxycycline, azithromycin, zinc), an effective amount of an agent is, for example, an amount sufficient to achieve alleviation or amelioration or prevention or prophylaxis of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; or amelioration or palliation of the disease, disorder, or condition (e.g., viral infection, etc.), whether detectable or undetectable, as compared to the response obtained without administration of the agent.

Typically, the treatment of a disease, disorder, or condition (e.g., the conditions described herein such as those associated with infection) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. Palliating a disease, disorder, or condition may indicate that the extent and/or undesirable clinical manifestations of the disease, disorder, or condition are lessened and/or time course of the progression is slowed or lengthened, as compared to the extent or time course in the absence of treatment.

Pharmaceutically effective regimens are typically systematic plans for the administration of one or more therapeutic agents, which includes aspects such as type of therapeutic agent, therapeutic agent concentrations, and any changes therein made during the course of the drug administration, which when administered is capable of (e.g., is effective in, etc.) treating and/or preventing an infection. Pharmaceutically effective regimens may include daily administration or a maximum administration for a period of time (e.g., one or more than one week such as one week, two weeks, three, weeks, four weeks, etc.). For example, the composition may be administered such that the quinoline derivative (e.g., chloroquine, hydroxychloroquine, quinine, quinidine, etc.) is administered one or more times daily and less than 1000 mg or less than 500 mg or less than 400 mg of less than 300 mg or less than 200 mg or less than 100 mg or less than 50 mg or less than 25 mg of the quinoline derivative is administered every day. In some embodiments, the composition may be administered such that the anti-viral agent (e.g., pyrithione, hinokitiol, tetracycline, doxycycline, azithromycin, zinc) is administered one or more times daily and less than 1000 mg or less than 500 mg or less than 400 mg of less than 300 mg or less than 200 mg or less than 100 mg or less than 50 mg or less than 25 mg of the quinoline derivative is administered every day. In some embodiments, the pharmaceutical composition may be formulated for the prevention of infection. In particular, the dose in the pharmaceutical composition for the prophylaxis of invention may comprise a dose of the quinoline derivative and/or the anti-viral agent that is less than the antibacterial dose of the same agent.

Any of the active agents described herein may be in the form of a prodrug which may be a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor. A prodrug may be synthesized using reactants other than the corresponding drug. For example, prodrug of an active agent may be in the form of an in vivo hydrolysable ester of the specified active agent.

Subject may refer to any organism to which a composition and/or compound in accordance with the disclosure may be administered, e.g., for experimental, diagnostic, prophylactic, and/or therapeutic purposes. Typical subjects include any animal (e.g., mammals such as mice, rats, rabbits, non-human primates, and humans, etc.). A subject in need thereof is typically a subject for whom it is desirable to treat a disease, disorder, or condition as described herein. For example, a subject in need thereof may seek or be in need of treatment, require treatment, be receiving treatment, may be receiving treatment in the future, or a human or animal that is under care by a trained professional for a particular disease, disorder, or condition.

Unless otherwise indicated, all references to concentrations include the indicated amounts on a weight by weight, weight by volume or volume by volume basis. Any reference to a percent concentration will be understood to refer to one of wt/wt, wt/vol, or wt/vol unless otherwise indicated. While certain embodiments may be described by concentrations as wt/wt or wt/vol, it should be understood that some compositions may have the same % on a wt/wt and wt/vol basis.

The pharmaceutical composition may comprise one or more pharmaceutically acceptable carrier, diluents, or excipients and a therapeutically effective amount of a quinoline derivative and an anti-viral agent;

wherein the anti-viral agent is selected from pyrithione, hinokitiol, tetracycline, doxycycline, azithromycin, and zinc; or tautomers, enantiomers, mixtures of enantiomers, racemates, thereof; or prodrugs thereof, or pharmaceutically acceptable salts of any of the foregoing;

wherein said pharmaceutical composition is an oral composition or a nasal composition. These anti-viral agents In some embodiments, the pharmaceutical composition may be in the form of a spray, ointment, foam, solution for producing heated steam, aerosol, liquid drops, mouthwash, mouth rinse, syrup, or tonic. In various implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) of the quinoline derivative. In some embodiments, the pharmaceutical composition comprises from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) of the anti-viral agent. For example, the pharmaceutical composition may comprise from 0.05 mg/mL to 5 mg/mL of the quinoline derivative and from 0.05 mg/mL to 5 mg/mL of the anti-viral agent. In various implementations, the pharmaceutical composition may have a weight ratio of the quinoline derivative to the anti-viral agent of 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). The quinoline derivative may be selected from, for example, chloroquine, hydroxychloroquine, quinine, or quinidine enantiomers, mixtures of enantiomers, racemates, thereof; or prodrugs thereof, or pharmaceutically acceptable salts of any of the foregoing.

In some embodiments, the composition may comprise either active (e.g., the quinoline derivative, the anti-viral selected from pyrithione, hinokitiol, tetracycline, doxycycline, azithromycin) independently in an amount of from 0.0001 mg/mL to 100 mg/mL (e.g., 0.001 to 50 mg/mL or 0.01 to 10 mg/mL, or 0.0001 mg/mL to 1 mg/mL, or 1 mg/mL to 10 mg/mL, or 0.0001 mg/mL to 0.001 mg/mL, or 0.001 mg/mL to 0.01 mg/mL, or 0.01 mg/mL to 0.1 mg/mL, or 0.1 mg/mL to 1 mg/mL, or 1 mg/mL to 10 mg/mL, etc.). In some embodiments, the composition may comprise from 0.000001% to 10% of either active by weight of the composition (e.g., 0.00001% to 5% by weight of the composition or 0.0001% to 1% by weight of the composition, or 0.00001% to 0.01% by weight of the composition, or 1% to 10% by weight of the composition, or 0.00001% to 0.0001% by weight of the composition, or 0.0001% to 0.001% by weight of the composition, or 0.0001% to 0.001% by weight of the composition, or 0.001% to 0.01% by weight of the composition, or 0.01% to 0.1% by weight of the composition, or 0.1% to 1% by weight of the composition, or 1% to 10% by weight of the composition, etc.).

The pharmaceutical composition (e.g., nasal spray, ointment, foam, liquid drop, mouthwash, solution for producing heated steam, mouth wash, etc.) may comprise chloroquine or prodrugs or pharmaceutically acceptable salts thereof as the quinoline derivative and pyrithione or prodrugs or pharmaceutically acceptable salts thereof as the anti-viral agent. In certain embodiments, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) chloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) pyrithione. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) chloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) pyrithione by weight of the composition. In various implementations, the pharmaceutical composition may comprise a weight ratio of chloroquine:pyrithione from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In various embodiments, the pharmaceutical composition may comprise less than 80 mg/1000 cc or less than 70 mg/1000 cc or less than 50 mg/1000 cc chloroquine. In certain implementations, the pharmaceutical composition may comprise less than 80 mg/1000 cc or less than 70 mg/1000 cc or less than 50 mg/1000 cc pyrithione. In some implementations, the pharmaceutical composition may comprise less than 80 mg/mL or less than 70 mg/mL or less than 50 mg/mL chloroquine. In various implementations, the pharmaceutical composition may comprise less than 80 mg/mL or less than 70 mg/mL or less than 50 mg/mL pyrithione. In various embodiments, the chloroquine and/or pyrithione may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise hydroxychloroquine or prodrugs or pharmaceutically acceptable salts thereof as the quinoline derivative and pyrithione or prodrugs or pharmaceutically acceptable salts thereof as the anti-viral agent. In some embodiments, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) hydroxychloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) pyrithione. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) hydroxychloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) pyrithione by weight of the composition. In some implementations, the pharmaceutical composition may comprise a weight ratio of hydroxychloroquine:pyrithione from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In some implementations, the pharmaceutical composition may comprise less than 80 mg/1000 cc or less than 70 mg/1000 cc or less than 50 mg/1000 cc hydroxychloroquine. In some implementations, the pharmaceutical composition may comprise less than 80 mg/1000 cc or less than 70 mg/1000 cc or less than 50 mg/1000 cc pyrithione. In various aspects, the pharmaceutical composition may comprise less than 80 mg/mL or less than 70 mg/mL or less than 50 mg/mL hydroxychloroquine. In some aspects, the pharmaceutical composition may comprise less than 80 mg/mL or less than 70 mg/mL or less than 50 mg/mL pyrithione. In various embodiments, the hydroxychloroquine and/or pyrithione may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinine or prodrugs or pharmaceutically acceptable salts thereof as the quinoline derivative and pyrithione or prodrugs or pharmaceutically acceptable salts thereof as the anti-viral agent. In some aspects, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) pyrithione. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) pyrithione by weight of the composition. In various embodiments, the pharmaceutical composition may comprise a weight ratio of quinine:pyrithione from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In various aspects, the pharmaceutical composition may comprise less than 80 mg/1000 cc or less than 70 mg/1000 cc or less than 50 mg/1000 cc quinine. In some implementations, the pharmaceutical composition may comprise less than 80 mg/1000 cc or less than 70 mg/1000 cc or less than 50 mg/1000 cc pyrithione. In various embodiments, the pharmaceutical composition may comprise less than 80 mg/mL or less than 70 mg/mL or less than 50 mg/mL quinine. In certain implementations, the pharmaceutical composition may comprise less than 80 mg/mL or less than 70 mg/mL or less than 50 mg/mL pyrithione. In various embodiments, the quinine and/or pyrithione may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinidine or prodrugs or pharmaceutically acceptable salts thereof as the quinoline derivative and pyrithione or prodrugs or pharmaceutically acceptable salts thereof as the anti-viral agent. In various implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinidine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) pyrithione. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinidine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) pyrithione by weight of the composition. In some implementations, the pharmaceutical composition may comprise a weight ratio of quinidine:pyrithione from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In various aspects, the pharmaceutical composition may comprise less than 80 mg/1000 cc or less than 70 mg/1000 cc or less than 50 mg/1000 cc quinidine. In various implementations, the pharmaceutical composition may comprise less than 80 mg/1000 cc or less than 70 mg/1000 cc or less than 50 mg/1000 cc pyrithione. In various implementations, the pharmaceutical composition may comprise less than 80 mg/mL or less than 70 mg/mL or less than 50 mg/mL quinidine. In various implementations, the pharmaceutical composition may comprise less than 80 mg/mL or less than 70 mg/mL or less than 50 mg/mL pyrithione. In certain embodiments, the quinidine and/or pyrithione may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise chloroquine or prodrugs or pharmaceutically acceptable salts thereof as the quinoline derivative and hinokitiol or prodrugs or pharmaceutically acceptable salts thereof as the anti-viral agent. In some implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) chloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) hinokitiol. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) chloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) hinokitiol by weight of the composition. In various embodiments, the pharmaceutical composition may comprise a weight ratio of chloroquine:hinokitiol from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain implementations, the pharmaceutical composition may comprise less than 80 mg/1000 cc or less than 70 mg/1000 cc or less than 50 mg/1000 cc chloroquine. In some embodiments, the pharmaceutical composition may comprise less than 80 mg/1000 cc or less than 70 mg/1000 cc or less than 50 mg/1000 cc hinokitiol. In some aspects, the pharmaceutical composition may comprise less than 80 mg/mL or less than 70 mg/mL or less than 50 mg/mL chloroquine. In certain implementations, the pharmaceutical composition may comprise less than 80 mg/mL or less than 70 mg/mL or less than 50 mg/mL hinokitiol. In various embodiments, the chloroquine and/or hinokitiol may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise hydroxychloroquine or prodrugs or pharmaceutically acceptable salts thereof as the quinoline derivative and hinokitiol or prodrugs or pharmaceutically acceptable salts thereof as the anti-viral agent. In some implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) hydroxychloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) hinokitiol. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) hydroxychloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) hinokitiol by weight of the composition. In certain embodiments, the pharmaceutical composition may comprise a weight ratio of hydroxychloroquine:hinokitiol from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain embodiments, the pharmaceutical composition may comprise less than 80 mg/1000 cc or less than 70 mg/1000 cc or less than 50 mg/1000 cc hydroxychloroquine. In certain embodiments, the pharmaceutical composition may comprise less than 80 mg/1000 cc or less than 70 mg/1000 cc or less than 50 mg/1000 cc hinokitiol. In various implementations, the pharmaceutical composition may comprise less than 80 mg/mL or less than 70 mg/mL or less than 50 mg/mL hydroxychloroquine. In certain aspects, the pharmaceutical composition may comprise less than 80 mg/mL or less than 70 mg/mL or less than 50 mg/mL hinokitiol. In some implementations, the hydroxychloroquine and/or hinokitiol may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinine or prodrugs or pharmaceutically acceptable salts thereof as the quinoline derivative and hinokitiol or prodrugs or pharmaceutically acceptable salts thereof as the anti-viral agent. In various implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) hinokitiol. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) hinokitiol by weight of the composition. In some implementations, the pharmaceutical composition may comprise a weight ratio of quinine:hinokitiol from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain implementations, the pharmaceutical composition may comprise less than 80 mg/1000 cc or less than 70 mg/1000 cc or less than 50 mg/1000 cc quinine. In some implementations, the pharmaceutical composition may comprise less than 80 mg/1000 cc or less than 70 mg/1000 cc or less than 50 mg/1000 cc hinokitiol. In certain implementations, the pharmaceutical composition may comprise less than 80 mg/mL or less than 70 mg/mL or less than 50 mg/mL quinine. In some implementations, the pharmaceutical composition may comprise less than 80 mg/mL or less than 70 mg/mL or less than 50 mg/mL hinokitiol. In certain implementations, the quinine and/or hinokitiol may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinidine or prodrugs or pharmaceutically acceptable salts thereof as the quinoline derivative and hinokitiol or prodrugs or pharmaceutically acceptable salts thereof as the anti-viral agent. In some implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinidine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) hinokitiol. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinidine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) hinokitiol by weight of the composition. In certain aspects, the pharmaceutical composition may comprise a weight ratio of quinidine:hinokitiol from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain embodiments, the pharmaceutical composition may comprise less than 80 mg/1000 cc or less than 70 mg/1000 cc or less than 50 mg/1000 cc quinidine. In certain aspects, the pharmaceutical composition may comprise less than 80 mg/1000 cc or less than 70 mg/1000 cc or less than 50 mg/1000 cc hinokitiol. In certain implementations, the pharmaceutical composition may comprise less than 80 mg/mL or less than 70 mg/mL or less than 50 mg/mL quinidine. In some embodiments, the pharmaceutical composition may comprise less than 80 mg/mL or less than 70 mg/mL or less than 50 mg/mL hinokitiol. In some aspects, the quinidine and/or hinokitiol may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise chloroquine or prodrugs or pharmaceutically acceptable salts thereof as the quinoline derivative and tetracycline or prodrugs or pharmaceutically acceptable salts thereof as the anti-viral agent. In some embodiments, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) chloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) tetracycline. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) chloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) tetracycline by weight of the composition. In some aspects, the pharmaceutical composition may comprise a weight ratio of chloroquine:tetracycline from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In some implementations, the pharmaceutical composition may comprise less than 80 mg/1000 cc or less than 70 mg/1000 cc or less than 50 mg/1000 cc chloroquine. In some implementations, the pharmaceutical composition may comprise less than 80 mg/1000 cc or less than 70 mg/1000 cc or less than 50 mg/1000 cc tetracycline. In some aspects, the pharmaceutical composition may comprise less than 80 mg/mL or less than 70 mg/mL or less than 50 mg/mL chloroquine. In some aspects, the pharmaceutical composition may comprise less than 80 mg/mL or less than 70 mg/mL or less than 50 mg/mL tetracycline. In certain aspects, the chloroquine and/or tetracycline may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise hydroxychloroquine or prodrugs or pharmaceutically acceptable salts thereof as the quinoline derivative and tetracycline or prodrugs or pharmaceutically acceptable salts thereof as the anti-viral agent. In various aspects, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) hydroxychloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) tetracycline. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) hydroxychloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) tetracycline by weight of the composition. In some aspects, the pharmaceutical composition may comprise a weight ratio of hydroxychloroquine:tetracycline from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In some embodiments, the pharmaceutical composition may comprise less than 80 mg/1000 cc or less than 70 mg/1000 cc or less than 50 mg/1000 cc hydroxychloroquine. In some aspects, the pharmaceutical composition may comprise less than 80 mg/1000 cc or less than 70 mg/1000 cc or less than 50 mg/1000 cc tetracycline. In certain implementations, the pharmaceutical composition may comprise less than 80 mg/mL or less than 70 mg/mL or less than 50 mg/mL hydroxychloroquine. In some embodiments, the pharmaceutical composition may comprise less than 80 mg/mL or less than 70 mg/mL or less than 50 mg/mL tetracycline. In various embodiments, the hydroxychloroquine and/or tetracycline may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinine or prodrugs or pharmaceutically acceptable salts thereof as the quinoline derivative and tetracycline or prodrugs or pharmaceutically acceptable salts thereof as the anti-viral agent. In certain implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) tetracycline. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) tetracycline by weight of the composition. In some embodiments, the pharmaceutical composition may comprise a weight ratio of quinine:tetracycline from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In some implementations, the pharmaceutical composition may comprise less than 80 mg/1000 cc or less than 70 mg/1000 cc or less than 50 mg/1000 cc quinine. In various implementations, the pharmaceutical composition may comprise less than 80 mg/1000 cc or less than 70 mg/1000 cc or less than 50 mg/1000 cc tetracycline. In some aspects, the pharmaceutical composition may comprise less than 80 mg/mL or less than 70 mg/mL or less than 50 mg/mL quinine. In some embodiments, the pharmaceutical composition may comprise less than 80 mg/mL or less than 70 mg/mL or less than 50 mg/mL tetracycline. In various embodiments, the quinine and/or tetracycline may be incorporated into a fabric filter such as cloth (e.g., by impregnation such as by bathing the filter in a solution comprising the active(s) followed by drying) such as used in surgical facemask including N95 facemasks.

The pharmaceutical composition (e.g., nasal spray, ointment, foam, liquid drop, mouthwash, solution for producing heated steam, mouth wash, etc.) may comprise quinidine or prodrugs or pharmaceutically acceptable salts thereof as the quinoline derivative and tetracycline or prodrugs or pharmaceutically acceptable salts thereof as the anti-viral agent. In some embodiments, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinidine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) tetracycline. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinidine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) tetracycline by weight of the composition. In some embodiments, the pharmaceutical composition may comprise a weight ratio of quinidine:tetracycline from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain aspects, the pharmaceutical composition may comprise less than 80 mg/1000 cc or less than 70 mg/1000 cc or less than 50 mg/1000 cc quinidine. In certain embodiments, the pharmaceutical composition may comprise less than 80 mg/1000 cc or less than 70 mg/1000 cc or less than 50 mg/1000 cc tetracycline. In various implementations, the pharmaceutical composition may comprise less than 80 mg/mL or less than 70 mg/mL or less than 50 mg/mL quinidine. In certain aspects, the pharmaceutical composition may comprise less than 80 mg/mL or less than 70 mg/mL or less than 50 mg/mL tetracycline. In certain aspects, the quinidine and/or tetracycline may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise chloroquine or prodrugs or pharmaceutically acceptable salts thereof as the quinoline derivative and doxycycline or prodrugs or pharmaceutically acceptable salts thereof as the anti-viral agent. In various implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) chloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) doxycycline. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) chloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) doxycycline by weight of the composition. In some aspects, the pharmaceutical composition may comprise a weight ratio of chloroquine:doxycycline from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In various implementations, the pharmaceutical composition may comprise less than 80 mg/1000 cc or less than 70 mg/1000 cc or less than 50 mg/1000 cc chloroquine. In certain aspects, the pharmaceutical composition may comprise less than 80 mg/1000 cc or less than 70 mg/1000 cc or less than 50 mg/1000 cc doxycycline. In certain embodiments, the pharmaceutical composition may comprise less than 80 mg/mL or less than 70 mg/mL or less than 50 mg/mL chloroquine. In some embodiments, the pharmaceutical composition may comprise less than 80 mg/mL or less than 70 mg/mL or less than 50 mg/mL doxycycline. In various embodiments, the chloroquine and/or doxycycline may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise hydroxychloroquine or prodrugs or pharmaceutically acceptable salts thereof as the quinoline derivative and doxycycline or prodrugs or pharmaceutically acceptable salts thereof as the anti-viral agent. In certain aspects, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) hydroxychloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) doxycycline. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) hydroxychloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) doxycycline by weight of the composition. In certain implementations, the pharmaceutical composition may comprise a weight ratio of hydroxychloroquine:doxycycline from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain aspects, the pharmaceutical composition may comprise less than 80 mg/1000 cc or less than 70 mg/1000 cc or less than 50 mg/1000 cc hydroxychloroquine. In various implementations, the pharmaceutical composition may comprise less than 80 mg/1000 cc or less than 70 mg/1000 cc or less than 50 mg/1000 cc doxycycline. In certain aspects, the pharmaceutical composition may comprise less than 80 mg/mL or less than 70 mg/mL or less than 50 mg/mL hydroxychloroquine. In certain embodiments, the pharmaceutical composition may comprise less than 80 mg/mL or less than 70 mg/mL or less than 50 mg/mL doxycycline. In some embodiments, the hydroxychloroquine and/or doxycycline may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinine or prodrugs or pharmaceutically acceptable salts thereof as the quinoline derivative and doxycycline or prodrugs or pharmaceutically acceptable salts thereof as the anti-viral agent. In certain embodiments, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) doxycycline. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) doxycycline by weight of the composition. In various embodiments, the pharmaceutical composition may comprise a weight ratio of quinine:doxycycline from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain aspects, the pharmaceutical composition may comprise less than 80 mg/1000 cc or less than 70 mg/1000 cc or less than 50 mg/1000 cc quinine. In various embodiments, the pharmaceutical composition may comprise less than 80 mg/1000 cc or less than 70 mg/1000 cc or less than 50 mg/1000 cc doxycycline. In some implementations, the pharmaceutical composition may comprise less than 80 mg/mL or less than 70 mg/mL or less than 50 mg/mL quinine. In certain implementations, the pharmaceutical composition may comprise less than 80 mg/mL or less than 70 mg/mL or less than 50 mg/mL doxycycline. In certain embodiments, the quinine and/or doxycycline may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinidine or prodrugs or pharmaceutically acceptable salts thereof as the quinoline derivative and doxycycline or prodrugs or pharmaceutically acceptable salts thereof as the anti-viral agent. In certain implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinidine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) doxycycline. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinidine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) doxycycline by weight of the composition. In certain implementations, the pharmaceutical composition may comprise a weight ratio of quinidine:doxycycline from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In various implementations, the pharmaceutical composition may comprise less than 80 mg/1000 cc or less than 70 mg/1000 cc or less than 50 mg/1000 cc quinidine. In some embodiments, the pharmaceutical composition may comprise less than 80 mg/1000 cc or less than 70 mg/1000 cc or less than 50 mg/1000 cc doxycycline. In some implementations, the pharmaceutical composition may comprise less than 80 mg/mL or less than 70 mg/mL or less than 50 mg/mL quinidine. In various implementations, the pharmaceutical composition may comprise less than 80 mg/mL or less than 70 mg/mL or less than 50 mg/mL doxycycline. In certain embodiments, the quinidine and/or doxycycline may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise chloroquine or prodrugs or pharmaceutically acceptable salts thereof as the quinoline derivative and azithromycin or prodrugs or pharmaceutically acceptable salts thereof as the anti-viral agent. In various embodiments, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) chloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) azithromycin. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) chloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) azithromycin by weight of the composition. In some implementations, the pharmaceutical composition may comprise a weight ratio of chloroquine:azithromycin from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In various implementations, the pharmaceutical composition may comprise less than 80 mg/1000 cc or less than 70 mg/1000 cc or less than 50 mg/1000 cc chloroquine. In some aspects, the pharmaceutical composition may comprise less than 80 mg/1000 cc or less than 70 mg/1000 cc or less than 50 mg/1000 cc azithromycin. In certain aspects, the pharmaceutical composition may comprise less than 80 mg/mL or less than 70 mg/mL or less than 50 mg/mL chloroquine. In various implementations, the pharmaceutical composition may comprise less than 80 mg/mL or less than 70 mg/mL or less than 50 mg/mL azithromycin. In certain embodiments, the chloroquine and/or azithromycin may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise hydroxychloroquine or prodrugs or pharmaceutically acceptable salts thereof as the quinoline derivative and azithromycin or prodrugs or pharmaceutically acceptable salts thereof as the anti-viral agent. In some implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) hydroxychloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) azithromycin. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) hydroxychloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) azithromycin by weight of the composition. In various implementations, the pharmaceutical composition may comprise a weight ratio of hydroxychloroquine:azithromycin from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In various implementations, the pharmaceutical composition may comprise less than 80 mg/1000 cc or less than 70 mg/1000 cc or less than 50 mg/1000 cc hydroxychloroquine. In some embodiments, the pharmaceutical composition may comprise less than 80 mg/1000 cc or less than 70 mg/1000 cc or less than 50 mg/1000 cc azithromycin. In various implementations, the pharmaceutical composition may comprise less than 80 mg/mL or less than 70 mg/mL or less than 50 mg/mL hydroxychloroquine. In various implementations, the pharmaceutical composition may comprise less than 80 mg/mL or less than 70 mg/mL or less than 50 mg/mL azithromycin. In certain embodiments, the hydroxychloroquine and/or azithromycin may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinine or prodrugs or pharmaceutically acceptable salts thereof as the quinoline derivative and azithromycin or prodrugs or pharmaceutically acceptable salts thereof as the anti-viral agent. In some implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) azithromycin. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) azithromycin by weight of the composition. In certain aspects, the pharmaceutical composition may comprise a weight ratio of quinine:azithromycin from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain implementations, the pharmaceutical composition may comprise less than 80 mg/1000 cc or less than 70 mg/1000 cc or less than 50 mg/1000 cc quinine. In some implementations, the pharmaceutical composition may comprise less than 80 mg/1000 cc or less than 70 mg/1000 cc or less than 50 mg/1000 cc azithromycin. In various implementations, the pharmaceutical composition may comprise less than 80 mg/mL or less than 70 mg/mL or less than 50 mg/mL quinine. In various implementations, the pharmaceutical composition may comprise less than 80 mg/mL or less than 70 mg/mL or less than 50 mg/mL azithromycin. In various aspects, the quinine and/or azithromycin may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinidine or prodrugs or pharmaceutically acceptable salts thereof as the quinoline derivative and azithromycin or prodrugs or pharmaceutically acceptable salts thereof as the anti-viral agent. In various implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinidine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) azithromycin. For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinidine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) azithromycin by weight of the composition. In certain implementations, the pharmaceutical composition may comprise a weight ratio of quinidine:azithromycin from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In various aspects, the pharmaceutical composition may comprise less than 80 mg/1000 cc or less than 70 mg/1000 cc or less than 50 mg/1000 cc quinidine. In certain implementations, the pharmaceutical composition may comprise less than 80 mg/1000 cc or less than 70 mg/1000 cc or less than 50 mg/1000 cc azithromycin. In certain aspects, the pharmaceutical composition may comprise less than 80 mg/mL or less than 70 mg/mL or less than 50 mg/mL quinidine. In various implementations, the pharmaceutical composition may comprise less than 80 mg/mL or less than 70 mg/mL or less than 50 mg/mL azithromycin. In various aspects, the quinidine and/or azithromycin may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise chloroquine or prodrugs or pharmaceutically acceptable salts thereof as the quinoline derivative and zinc (e.g., zinc, compounds which comprise zinc which may release zinc ions in vivo, $ZnO_2$, etc.) or prodrugs or pharmaceutically acceptable salts thereof as the anti-viral agent. In various aspects, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) chloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) zinc (e.g., zinc, compounds which comprise zinc which may release zinc ions in vivo, $ZnO_2$, etc.). For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) chloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) zinc (e.g., zinc, compounds which comprise zinc which may release zinc ions in vivo, $ZnO_2$, etc.) by weight of the composition. In some embodiments, the pharmaceutical composition may comprise a weight ratio of chloroquine:zinc (e.g., zinc, compounds which comprise zinc which may release zinc ions in vivo, $ZnO_2$, etc.) from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain aspects, the pharmaceutical composition may comprise less than 80 mg/1000 cc or less than 70 mg/1000 cc or less than 50 mg/1000 cc chloroquine. In some aspects, the pharmaceutical composition may comprise less than 80 mg/1000 cc or less than 70 mg/1000 cc or less than 50 mg/1000 cc zinc (e.g., zinc, compounds which comprise zinc which may release zinc ions in vivo, $ZnO_2$, etc.). In certain aspects, the pharmaceutical composition may comprise less than 80 mg/mL or less than 70 mg/mL or less than 50 mg/mL chloroquine. In various implementations, the pharmaceutical composition may comprise less than 80 mg/mL or less than 70 mg/mL or less than 50 mg/mL zinc (e.g., zinc, compounds which comprise zinc which may release zinc ions in vivo, $ZnO_2$, etc.). In various embodiments, the chloroquine and/or zinc (e.g., zinc, compounds which comprise zinc which may release zinc ions in vivo, $ZnO_2$, etc.) may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise hydroxychloroquine or prodrugs or pharmaceutically acceptable salts thereof as the quinoline derivative and zinc (e.g., zinc, compounds which comprise zinc which may release zinc ions in vivo, $ZnO_2$, etc.) or prodrugs or pharmaceutically acceptable salts thereof as the anti-viral agent. In certain aspects, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) hydroxychloroquine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) zinc (e.g., zinc, compounds which comprise zinc which may release zinc ions in vivo, $ZnO_2$, etc.). For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) hydroxychloroquine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) zinc (e.g., zinc, compounds which comprise zinc which may release zinc ions in vivo, $ZnO_2$, etc.) by weight of the composition. In certain implementations, the pharmaceutical composition may comprise a weight ratio of hydroxychloroquine:zinc (e.g., zinc, compounds which comprise zinc which may release zinc ions in vivo, $ZnO_2$, etc.) from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain embodiments, the pharmaceutical composition may comprise less than 80 mg/1000 cc or less than 70 mg/1000 cc or less than 50 mg/1000 cc hydroxychloroquine. In certain embodiments, the pharmaceutical composition may comprise less than 80 mg/1000 cc or less than 70 mg/1000 cc or less than 50 mg/1000 cc zinc (e.g., zinc, compounds which comprise zinc which may release zinc ions in vivo, $ZnO_2$, etc.). In certain embodiments, the pharmaceutical composition may comprise less than 80 mg/mL or less than 70 mg/mL or less than 50 mg/mL hydroxychloroquine. In certain aspects, the pharmaceutical composition may comprise less than 80 mg/mL or less than 70 mg/mL or less than 50 mg/mL zinc (e.g., zinc, compounds which comprise zinc which may release zinc ions in vivo, $ZnO_2$, etc.). In various aspects, the hydroxychloroquine and/or zinc (e.g., zinc, compounds which comprise zinc which may release zinc ions in vivo, $ZnO_2$, etc.) may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinine or prodrugs or pharmaceutically acceptable salts thereof as the quinoline derivative and zinc (e.g., zinc, compounds which comprise zinc which may release zinc ions in vivo, $ZnO_2$, etc.) or prodrugs or pharmaceutically acceptable salts thereof as the anti-viral agent. In various embodiments, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) zinc (e.g., zinc, compounds which comprise zinc which may release zinc ions in vivo, $ZnO_2$, etc.). For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) zinc (e.g., zinc, compounds which comprise zinc which may release zinc ions in vivo, $ZnO_2$, etc.) by weight of the composition. In certain embodiments, the pharmaceutical composition may comprise a weight ratio of quinine:zinc (e.g., zinc, compounds which comprise zinc which may release zinc ions in vivo, $ZnO_2$, etc.) from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In certain aspects, the pharmaceutical composition may comprise less than 80 mg/1000 cc or less than 70 mg/1000 cc or less than 50 mg/1000 cc quinine. In certain implementations, the pharmaceutical composition may comprise less than 80 mg/1000 cc or less than 70 mg/1000 cc or less than 50 mg/1000 cc zinc (e.g., zinc, compounds which comprise zinc which may release zinc ions in vivo, $ZnO_2$, etc.). In various embodiments, the pharmaceutical composition may comprise less than 80 mg/mL or less than 70 mg/mL or less than 50 mg/mL quinine. In some aspects, the pharmaceutical composition may comprise less than 80 mg/mL or less than 70 mg/mL or less than 50 mg/mL zinc (e.g., zinc, compounds which comprise zinc which may release zinc ions in vivo, $ZnO_2$, etc.). In various aspects, the quinine and/or zinc (e.g., zinc, compounds which comprise zinc which may release zinc ions in vivo, $ZnO_2$, etc.) may be incorporated into a fabric filter such as cloth (e.g., by impregnation such as by bathing the filter in a solution comprising the active(s) followed by drying) such as those used in surgical facemask including N95 facemasks.

The pharmaceutical composition (e.g., nasal spray, ointment, foam, liquid drop, mouthwash, solution for producing heated steam, mouth wash, etc.) may comprise quinidine or prodrugs or pharmaceutically acceptable salts thereof as the quinoline derivative and zinc (e.g., zinc, compounds which comprise zinc which may release zinc ions in vivo, $ZnO_2$, etc.) or prodrugs or pharmaceutically acceptable salts thereof as the anti-viral agent. In certain implementations, the pharmaceutical composition may comprise from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) quinidine and from 0.01 mg/mL to 5 mg/mL (e.g., from 0.05 mg/mL to 5 mg/mL, from 0.05 mg/mL to 0.1 mg/mL, from 0.1 mg/mL to 0.25 mg/mL, from 0.25 mg/mL to 0.5 mg/mL, from 0.5 mg/mL to 0.75 mg/mL, from 0.75 mg/mL to 1 mg/mL, 1 mg/mL to 2 mg/mL, 2 mg/mL to 3 mg/mL, 3 mg/mL to 4 mg/mL, 4 mg/mL to 5 mg/mL, etc.) zinc (e.g., zinc, compounds which comprise zinc which may release zinc ions in vivo, $ZnO_2$, etc.). For example, the pharmaceutical composition may comprise from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) quinidine by weight of the composition and from 1% to 99% (e.g., from 5% to 10%, from 10% to 20%, from 20% to 35%, from 35% to 45%, from 45% to 50%, from 50% to 70%, from 70% to 75%, from 75% to 80%, from 80% to 90%) zinc (e.g., zinc, compounds which comprise zinc which may release zinc ions in vivo, $ZnO_2$, etc.) by weight of the composition. In some aspects, the pharmaceutical composition may comprise a weight ratio of quinidine:zinc (e.g., zinc, compounds which comprise zinc which may release zinc ions in vivo, $ZnO_2$, etc.) from 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In some aspects, the pharmaceutical composition may comprise less than 80 mg/1000 cc or less than 70 mg/1000 cc or less than 50 mg/1000 cc quinidine. In various embodiments, the pharmaceutical composition may comprise less than 80 mg/1000 cc or less than 70 mg/1000 cc or less than 50 mg/1000 cc zinc (e.g., zinc, compounds which comprise zinc which may release zinc ions in vivo, $ZnO_2$, etc.). In various aspects, the pharmaceutical composition may comprise less than 80 mg/mL or less than 70 mg/mL or less than 50 mg/mL quinidine. In various implementations, the pharmaceutical composition may comprise less than 80 mg/mL or less than 70 mg/mL or less than 50 mg/mL zinc (e.g., zinc, compounds which comprise zinc which may release zinc ions in vivo, $ZnO_2$, etc.). In various implementations, the quinidine and/or zinc (e.g., zinc, compounds which comprise zinc which may release zinc ions in vivo, $ZnO_2$, etc.) may be incorporated into a fabric filter such as cloth (e.g., by impregnation such as by bathing the filter in a solution comprising the active(s) followed by drying) such as those used in surgical facemask including N95 facemasks.

Fabrics are also provided comprising a quinoline derivative and/or an anti-viral agent. These agents may be impregnated into the fabric. For example, an untreated fabric may be submerged in a solution comprising one or more of the quinoline derivatives and/or anti-viral agents in order to impregnate the fabric with the active material(s). The fabric may be then be dried to remove any residual solvent from the solution. In various embodiments, the anti-viral agent is selected from pyrithione, hinokitiol, tetracycline, doxycycline, azithromycin, and zinc; or tautomers, enantiomers, mixtures of enantiomers, racemates, thereof; or prodrugs thereof, or pharmaceutically acceptable salts of any of the foregoing. The quinoline derivative may be selected from, for example, chloroquine, hydroxychloroquine, quinine, or quinidine enantiomers, mixtures of enantiomers, racemates, thereof; or prodrugs thereof, or pharmaceutically acceptable salts of any of the foregoing. In several implementations, the fabric may be cloth (e.g., activated carbon cloth). In some embodiments, the fabric comprises from 0.05% to 50% (e.g., 0.5% to 10%, 10% to 20%, 20% to 30%, 30% to 40%, 40% to 50%, etc.) of the anti-viral agent or quinoline derivative by weight of the fabric. In various implementations, the fabric may comprise from about 0.1% to 20% of the anti-viral agent and quinoline derivative by weight of the fabric. For example, the fabric may have a weight ratio of the quinoline derivative to the anti-viral agent of 100:1 to 1:100 (e.g., from 50:1 to 1:50, from 25:1 to 1:25, from 10:1 to 1:10, from 5:1 to 1:5, from 2:1 to 1:2, from 100:1 to 1:1, from 50:1 to 1:1, from 25:1 to 1:1, from 10:1 to 1:1, from 5:1 to 1:1, from 1:1 to 1:100, from 1:1 to 1:50, from 1:1 to 1:25, from 1:1 to 1:10, from 1:1 to 1:5, from 100:1 to 50:1, from 50:1 to 25:1 from 25:1 to 10:1, from 10:1 to 5:1, from 5:1 to 2:1, from 2:1 to 1:2, from 1:2 to 1:5, from 1:5 to 1:10, from 1:10 to 1:25, from 1:25 to 1:50, from 1:50 to 1:100, etc.). In some embodiments, the fabric may have a thickness from 0.1 mm to 5 mm. The fabrics generally have an air breathability associated with surgical facemasks such that a user is able to, via breathing, move air through the fabric. In various implementations, the fabric has an air permeability of more than 1 $cm^3/cm^2/sec$ (e.g., as determined by ASTM D737-96, etc.) or more than 5 $cm^3/cm^2/sec$ (e.g., from 5 $cm^3/cm^2/sec$ to 100 $cm^3/cm^2/sec$ or from 5 $cm^3/cm^2/sec$ to 50 $cm^3/cm^2/sec$ or from 5 $cm^3/cm^2/sec$ to 20 $cm^3/cm^2/sec$ or from 5 $cm^3/cm^2/sec$ to 10 $cm^3/cm^2/sec$).

The fabric may also be used in a composite fabric. For example, the composite fabric may comprise the anti-viral and/or quinoline treated derivative fabric and one or more other layers attached thereto. In certain embodiments, the composite fabric has a waterproof layer (e.g., a polyurethane layer) attached to one surface and/or a breathable woven textile attached to a surface (e.g., the surface opposite the waterproof layer).

Facemasks are also disclosed having a breathing piece such that air passes through the breathing piece when a user is breathing; wherein the breathing piece comprises one or more fabrics as described herein.

Method of use for these devices are also provided. In some embodiments, the method may be for the treatment or prophylaxis of a viral infection or a disease, disorder, or condition associated with the viral infection in a subject in need thereof and may comprise administration of the pharmaceutical composition. In some embodiments, the pharmaceutical composition decreases the viral load of the infection in the subject. In various implementations, the pharmaceutical composition may prevent an increase in the viral load in the subject when the subject is exposed to the virus of the viral infection. In some embodiments, the viral infection may be coronavirus (e.g., HCoV-0C43, HKU1, NCoV-NL63, HCoV-229E, MERS-CoV, SARS-CoV, SARS-CoV-2, etc.).

The methods may be used to treat or to prevent the diseases, disorders, conditions, or symptoms resulting from viral infection. For example, coronaviruses often cause colds with major symptoms, such as fever, and sore throat from swollen adenoids, each of which the pharmaceutical compositions may treat or prevent. Furthermore, coronaviruses can cause pneumonia (either direct viral pneumonia or a secondary bacterial pneumonia) or bronchitis (either direct viral bronchitis or a secondary bacterial bronchitis). Coronaviruses may also cause severe acute respiratory syndrome (SARS), has a unique pathogenesis because it causes both upper and lower respiratory tract infections. These symptoms occur when the viral infection passes a threshold viral load. Without wishing to be bound by theory, oral application of the actives described herein prevents an increase in the viral loads in subjects administered these compounds, which may prevent the development of the symptoms associated with viral infection.

In some embodiments, administration of the therapeutic agents is delivered locally or regionally (e.g., intranasally, etc.). In some embodiments, a device is used to deliver the composition to the respiratory tract. The composition may be delivered through use of an inhaler, atomizer, nebulizer, nasal spray bottle, nasal spray pump, ventilator, compressed air tank, aerosolizer, and nasal cannula. The composition can be delivered through insufflation, inhalation, oral ingestion, sublingual, and any combination thereof.

At present the oral or nasal spray or aerosol route (e.g., by inhalation) is most commonly used to deliver therapeutic agents directly to the lungs and respiratory system. However, the invention encompasses the delivery of the inventive pharmaceutical composition by any appropriate route taking into consideration likely advances in the sciences of drug delivery. In some embodiments, preparations for inhaled or aerosol delivery comprise a plurality of particles. Such may have a mean particle size of from more than 1 micron (e.g., 4 microns, 5 microns, 6 microns, 7 microns, 8 microns, 9 microns, 10 microns, 11 microns, 12 microns, 13 microns, 4-20 microns, 5-20 microns, 6-20 microns, 7-20 microns, 8-20 microns, 9-20 microns, 10-20 microns, 11-20 microns, 12-20 microns, 13-20 microns, etc.) which may be determined by dynamic light scattering. In various embodiments, preparations for inhaled or aerosol delivery are formulated as a dry powder. In some embodiments, preparations for inhaled or aerosol delivery are formulated as a wet powder, for example through inclusion of a wetting agent. in some embodiments, the wetting agent is selected from the group consisting of water, saline, or other liquid of physiological pH.

In some embodiments, the pharmaceutical compositions are administered as drops to the nasal or buccal cavity. In some embodiments, a dose may comprise a plurality of drops (e.g., 1-100, 1-50, 1-20, 1-10, 1-5, etc.).

Pharmaceutical products for such administration are also provided. In some embodiments, the pharmaceutical product may comprise:
(a) a body configured to be inserted into a nasal passage for dispensing a nasal spray composition through an orifice;
(b) a reservoir in fluid communication with said orifice, wherein said nasal pharmaceutical composition is contained in said reservoir;
(c) a pump mechanism capable of expelling said nasal spray composition through said orifice in appropriate sized aerosolized droplets; capable of coating the nasal mucosa of a user;

wherein said nasal spray composition comprises:
a quinoline derivative and an anti-viral agent; and
a pharmaceutically acceptable carrier, diluent and/or excipient.

The pharmaceutical product may expel from 1 to 50 mL of the pharmaceutical composition (e.g., from 5 to 40 mL, from 10 to 30 mL, etc.).

In some embodiments, the pharmaceutical composition is in the form of an oral spray. Pharmaceutical products for oral administration are provided. In some embodiments, the pharmaceutical product may comprise:
(a) a body configured to be inserted into a nasal passage for dispensing a nasal spray composition through an orifice;
(b) a reservoir in fluid communication with said orifice, wherein said nasal pharmaceutical composition is contained in said reservoir;
(c) a pump mechanism capable of expelling said nasal spray composition through said orifice in appropriate sized aerosolized droplets; capable of coating the nasal mucosa of a user;

wherein said nasal spray composition comprises:
a quinoline derivative and an anti-viral agent; and
a pharmaceutically acceptable carrier, diluent and/or excipient.

The pharmaceutical product may expel from 1 to 50 mL of the pharmaceutical composition (e.g., from 5 to 40 mL, from 10 to 30 mL, etc.)

Additionally, methods of preventing the increase in the viral load in a subject in need thereof may comprise providing an anti-viral agent and/or quinoline derivative treated fabric or a facemask comprising these treated fabrics to the subject, wherein the subject breathes through the fabric thereby reducing the viral load passing into the respiratory system of the subject. In some embodiments, the method of preventing the increase in the viral load in a subject in need thereof may comprise wearing the treated fabric or the facemask comprising the treated fabric, such that wearing the facemask or fabric results in a configuration where the subject breathes through the fabric thereby reducing the viral load passing into the respiratory system of the subject. In some embodiments, wearing may include removably attaching the facemask and/or the fabric to the face such that the breathing piece is oriented proximal to the mouth and nose such that the air must pass through or on the treated fabric for the user to breathe. In some embodiments, the facemask is dimensioned to covers both the mouth and the nose of a user.

In any of the above aspects or embodiments, the method may reduce the growth of a viral infection, shrink the infection, or eradicate the infection. For example, the number of virions may decrease by more than 5%, more than 10%, more than 25%, more than 50%, more than 75%, more than 85%, more than 90%, more than 95%, or more than 99% as compared to its original size (e.g., as measured in vitro) following an administration regimen (e.g., daily, etc.). In some embodiments, the number of virions in a treated sample or subject may be less than 99% or less than 95% or less than 90% or less than 75% or less than 50% or less than 25% or less than 10% or less than 5% of the number of virions in an untreated control (i.e., an otherwise identical untreated subject or sample). In some embodiments, the indicated reduction or decrease may be measured at one or more post inoculation (e.g., one day, two days, three days, four days, five days, etc.).

SPECIFIC EMBODIMENTS

Non-limiting specific embodiments are described below each of which is considered to be within the present disclosure.

Specific Embodiment 1. A pharmaceutical composition comprising one or more pharmaceutically acceptable carrier, diluents, or excipients and a therapeutically effective amount of a quinoline derivative and optionally an anti-viral agent; wherein the anti-viral agent is selected from pyrithione, hinokitiol, tetracycline, doxycycline, azithromycin, and zinc; or tautomers, enantiomers, mixtures of enantiomers, racemates, thereof; or prodrugs thereof, or pharmaceutically acceptable salts of any of the foregoing.

Specific Embodiment 2. The pharmaceutical composition according to Specific Embodiment 1, wherein the composition is in a form suitable for oral administration.

Specific Embodiment 3. The pharmaceutical composition according to Specific Embodiment 1, wherein the composition is in a form suitable for intranasal administration.

Specific Embodiment 4. The pharmaceutical composition according to Specific Embodiment 1, wherein the composition is in a form suitable for administration to the eye (ocular), ear canal, or other mucosal and non-mucosal body surfaces.

Specific Embodiment 5. The pharmaceutical composition according to Specific Embodiment 1, wherein the pharmaceutical composition is in the form of a spray, ointment, foam, solution for producing steam (e.g., heated steam, cooled steam), aerosol, liquid drops, nasal spray, oral spray, mouthwash, mouth rinse, eye drops, ear drops, syrup, or tonic.

Specific Embodiment 6. The pharmaceutical composition according to Specific Embodiment 1 or 4, wherein the pharmaceutical composition comprises from 0.001 mg/mL to 5 mg/mL of the quinoline derivative.

Specific Embodiment 7. The pharmaceutical composition according to Specific Embodiment 1 or 4, wherein the pharmaceutical composition comprises from 0.001 mg/mL to 5 mg/mL of the anti-viral agent.

Specific Embodiment 8. The pharmaceutical composition according to Specific Embodiment 1 or 4, wherein the pharmaceutical composition comprises from 0.001 mg/mL to 5 mg/mL of said quinoline derivative and from 0.001 mg/mL to 5 mg/mL of the anti-viral agent.

Specific Embodiment 9. The pharmaceutical composition according to any one of Specific Embodiments 1-8, wherein the pharmaceutical composition has a weight ratio of the quinoline derivative to the anti-viral agent of 100:1 to 1:100.

Specific Embodiment 10. The pharmaceutical composition according to any one of Specific Embodiments 1-9, wherein the quinoline derivative is selected from chloroquine, hydroxychloroquine, quinine, or quinidine enantiomers, mixtures of enantiomers, racemates, thereof; or prodrugs thereof, or pharmaceutically acceptable salts of any of the foregoing.

Specific Embodiment 11. A fabric comprising a quinoline derivative and/or an anti-viral agent; wherein the anti-viral agent is selected from pyrithione, hinokitiol, tetracycline, doxycycline, azithromycin, and zinc; or tautomers, enantiomers, mixtures of enantiomers, racemates, thereof; or prodrugs thereof, or pharmaceutically acceptable salts of any of the foregoing; wherein the anti-viral agent and/or quinoline derivative is impregnated in the fabric.

Specific Embodiment 12. The fabric according to Specific Embodiment 10, wherein the fabric is cloth (e.g., activated carbon cloth).

Specific Embodiment 13. The fabric according to Specific Embodiment 10 or 11, wherein the fabric comprises from 0.01% to 10% of the anti-viral agent or quinoline derivative by weight of the fabric.

Specific Embodiment 14. The fabric according to any one of Specific Embodiments 10-12, wherein the fabric comprises from about 0.1% to 20% of the anti-viral agent and quinoline derivative by weight of the fabric.

Specific Embodiment 15. The fabric according to any one of Specific Embodiments 10-13, wherein the fabric has a weight ratio of the quinoline derivative to the anti-viral agent of 100:1 to 1:100.

Specific Embodiment 16. The fabric according to any one of Specific Embodiments 10-14, wherein the quinoline derivative is selected from chloroquine, hydroxychloroquine, quinine, or quinidine enantiomers, mixtures of enantiomers, racemates, thereof; or prodrugs thereof, or pharmaceutically acceptable salts of any of the foregoing.

Specific Embodiment 17. The fabric according to any one of Specific Embodiments 10-15, wherein the fabric has a thickness from 0.1 mm to 5 mm.

Specific Embodiment 18. The fabric according to any one of Specific Embodiments 10-16, wherein the fabric has an air permeability of more than 5 $cm^3/cm^2/sec$ (e.g., as determined by ASTM D737-96, etc.) (e.g., from 5 $cm^3/cm^2/sec$ to 100 $cm^3/cm^2/sec$ or from 5 $cm^3/cm^2/sec$ to 50 $cm^3/cm^2/sec$ or from 5 $cm^3/cm^2/sec$ to 20 $cm^3/cm^2/sec$ or from 5 $cm^3/cm^2/sec$ to 10 $cm^3/cm^2/sec$).

Specific Embodiment 19. The fabric according to any one of Specific Embodiments 11-18, wherein the fabric is a non-woven fabric.

Specific Embodiment 20. The fabric according to any one of Specific Embodiments 11-18, wherein the fabric is a woven fabric.

Specific Embodiment 21. A facemask having a breathing piece such that air passes through the breathing piece when a user is breathing; wherein the breathing piece comprises the fabric according to any one of Specific Embodiments 11-20 and the air passes through the fabric or moves along the surface of the fabric.

Specific Embodiment 22. A method for the treatment or prophylaxis of a viral infection or a disease, disorder, or condition associated with the viral infection in a subject in need thereof comprising administration of the pharmaceutical composition according to any one of Specific Embodiments 1-10 to the subject (e.g., nasal administration).

Specific Embodiment 23. The method according to Specific Embodiment 21, wherein the administration of the pharmaceutical composition decreases the viral load of the infection in the subject.

Specific Embodiment 24. The method according to Specific Embodiment 21, wherein the administration of the pharmaceutical composition prevents an increase in the viral load in the subject when the subject is exposed to the virus of the viral infection.

Specific Embodiment 25. The method according to any one of Specific Embodiments 22-24, wherein the viral infection is caused by coronavirus (e.g., HCoV-0C43, HKU1, NCoV-NL63, HCoV-229E, MERS-CoV, SARS-CoV, SARS-CoV-2, etc.).

Specific Embodiment 26. A method of preventing the contact of a virus with the oral or nasal mucosa in a subject in need thereof comprising providing the fabric according to any one of Specific Embodiments 11-20 or the facemask according to Specific Embodiment 20 to the subject, wherein the subject breathes through the fabric thereby reducing the viral load passing into the respiratory system of the subject.

Specific Embodiment 27. A method of preventing the contact of a virus with the oral or nasal mucosa in a subject in need thereof comprising wearing of the fabric according to any one of Specific Embodiments 11-21 or the facemask according to Specific Embodiment 21 to the subject, wherein the wearing results in a configuration where subject breathes through the fabric thereby reducing the viral load passing into the respiratory system of the subject.

Specific Embodiment 28. A method for prophylaxis against a respiratory infection comprising administering orally or intranasally to a subject in need thereof a pharmaceutical composition comprising a quinoline derivative and optionally an anti-viral agent;
wherein the anti-viral agent is selected from pyrithione, hinokitiol, tetracycline, doxycycline, azithromycin, and zinc; or tautomers, enantiomers, mixtures of enantiomers, racemates, thereof; or prodrugs thereof, or pharmaceutically acceptable salts of any of the foregoing.

Specific Embodiment 29 A method for prophylaxis against an infection comprising administering via mucosal or other body surfaces to a subject in need thereof a pharmaceutical composition comprising a quinoline derivative and an anti-viral agent;
wherein the anti-viral agent is selected from pyrithione, hinokitiol, tetracycline, doxycycline, azithromycin, and zinc; or tautomers, enantiomers, mixtures of enantiomers, racemates, thereof; or prodrugs thereof, or pharmaceutically acceptable salts of any of the foregoing.

Specific Embodiment 30. The method according to Specific Embodiment 29, wherein the mucosal or other body surfaces are selected from the eyes, ear canal, anus, and vagina.

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications and variances which fall within the scope of the appended claims.

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the disclosure.

The invention claimed is:

1. A pharmaceutical composition comprising one or more pharmaceutically acceptable carrier, diluents, or excipients and a therapeutically effective amount of a quinoline derivative and optionally an anti-viral agent;
wherein the quinoline derivative is selected from chloroquine, hydroxychloroquine, quinine, or quinidine, enantiomers, mixtures of enantiomers, racemates, thereof; or pharmaceutically acceptable salts of any of the foregoing; and
wherein the anti-viral agent is selected from pyrithione, hinokitiol, tetracycline, doxycycline, azithromycin, and zinc; or tautomers, enantiomers, mixtures of enantiomers, racemates, thereof or pharmaceutically acceptable salts of any of the foregoing.

2. The pharmaceutical composition according to claim 1, wherein the composition is in a form suitable for oral administration.

3. The pharmaceutical composition according to claim 1, wherein the composition is in a form suitable for intranasal administration.

4. The pharmaceutical composition according to claim 1, wherein the pharmaceutical composition is in the form of a spray, ointment, foam, solution for producing steam, aerosol, liquid drops, nasal spray, oral spray, mouthwash, mouth rinse, eye drops, ear drops, syrup, or tonic.

5. The pharmaceutical composition according to claim 1, wherein the pharmaceutical composition has a weight ratio of the quinoline derivative to the anti-viral agent of 100:1 to 1:100.

6. A fabric comprising a quinoline derivative and/or an anti-viral agent;
wherein the anti-viral agent is selected from pyrithione, hinokitiol, tetracycline, doxycycline, azithromycin, and zinc; or tautomers, enantiomers, mixtures of enantiomers, racemates, thereof, or pharmaceutically acceptable salts of any of the foregoing;
wherein the quinoline derivative is selected from chloroquine, hydroxychloroquine, quinine, or quinidine, enantiomers, mixtures of enantiomers, racemates, thereof; or pharmaceutically acceptable salts of any of the foregoing; and
wherein the anti-viral agent and/or quinoline derivative is impregnated in the fabric.

7. The fabric according to claim 6, wherein the fabric is cloth.

8. The fabric according to claim 6, wherein the fabric comprises from 0.01% to 10% of the anti-viral agent or quinoline derivative by weight of the fabric.

9. The fabric according to claim 6, wherein the fabric comprises from about 0.1% to 20% of the anti-viral agent and quinoline derivative by weight of the fabric.

10. The fabric according to claim 6, wherein the fabric has a weight ratio of the quinoline derivative to the anti-viral agent of 100:1 to 1:100.

11. The fabric according to claim 6, wherein the fabric has a thickness from 0.1 mm to 5 mm.

12. The fabric according to claim 6, wherein the fabric has an air permeability of more than 5 $cm^3/cm^2/sec$.

13. A facemask having a breathing piece such that air passes through the breathing piece when a user is breathing; wherein the breathing piece comprises the fabric according to claim 6, and the air passes through the fabric or moves along the surface of the fabric.

* * * * *